United States Patent [19]

Husbands

[11] 4,183,359
[45] Jan. 15, 1980

[54] EPILATOR

[75] Inventor: Harmon G. Husbands, Dallas, Tex.

[73] Assignee: Electro-Kinetic Eng./Mfg., Inc., Richardson, Tex.

[21] Appl. No.: 870,864

[22] Filed: Jan. 20, 1978

[51] Int. Cl.² .............................................. A61N 3/04
[52] U.S. Cl. ........................... 128/303.13; 128/303.17
[58] Field of Search ................... 128/303.13–303.19, 128/355, 381, 384, 411, 2.1 C; 174/5 SB, 5 SG; 219/223, 234; 361/220

[56] References Cited

U.S. PATENT DOCUMENTS

| 2,417,530 | 3/1947 | Weiser | 128/303.13 |
| 3,745,412 | 7/1973 | Ruff | 361/220 |
| 3,870,047 | 3/1975 | Gonser | 128/303.14 |
| 3,939,841 | 2/1976 | Dohring et al. | 128/303.19 |
| 3,999,552 | 12/1976 | Huggins | 128/303.13 |

FOREIGN PATENT DOCUMENTS

| 1536272 | 8/1968 | France | 128/303.17 |
| 438422 | 1/1975 | U.S.S.R. | 128/303.13 |

*Primary Examiner*—Lee S. Cohen
*Attorney, Agent, or Firm*—Hubbard, Thurman, Turner, Tucker & Glaser

[57] ABSTRACT

An epilator system is disclosed, of the type having a radio frequency source connected by a shielded cable to the tip of a tweezer. Improved operation is provided by a ground lead connected from the cable shield to a finger ring worn by the operator of the system.

4 Claims, 1 Drawing Figure

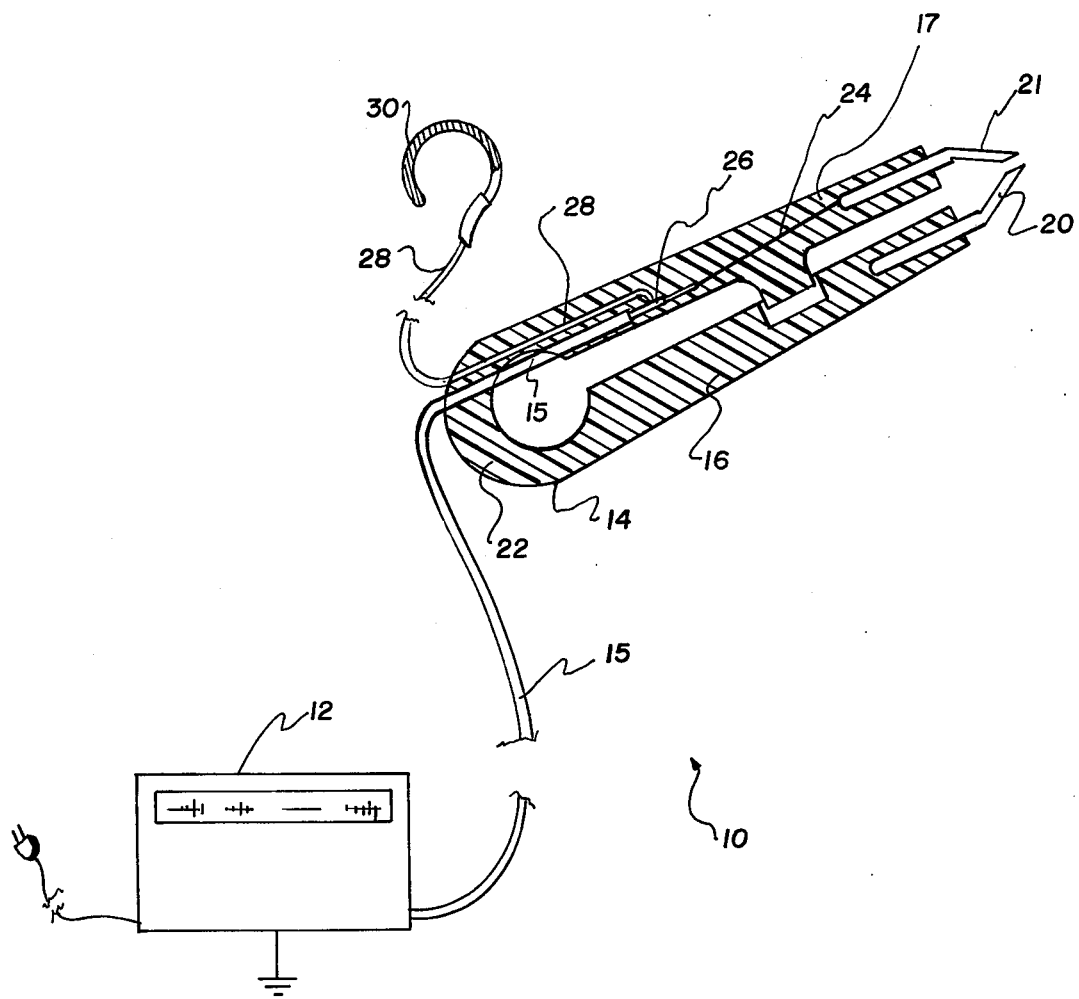

EPILATOR

BACKGROUND OF THE INVENTION

This invention relates to an improved epilator of the type in which radio frequency energy is applied to a hair through a tweezer.

For many years, the removal of superfluous hair by high frequency coagulation of the root required a needle to be inserted into the follicle containing the unwanted hair. The needle was energized by high frequency electrical energy which coagulated the hair papilla and, thus, killed the hair root after which the hair could be plucked from the follicle. This process was very difficult to control and could result in tissue damage by the insertion of the needle. Moreover, it was painful.

Another type of epilator, disclosed in U.S. Pat. Nos. 2,888,927 and 3,999,552, provided for the hair to be gripped by a tweezers connected to a radio frequency generator. When the tweezers are energized, the radio frequency energy generates heat in the growth area of the hair, and the hair can be readily removed without pain. With this type of device, the hair is gripped away from the skin and there is no necessity to insert any instrument into the follicle. This type of device avoids the sources of pain and injury that are possible by other methods of hair removal.

SUMMARY OF THE INVENTION

In accordance with the present invention, there is provided an improvement of the tweezer or gripper type of epilator that results in further improved speed and comfort. In this type of epilator system, a shielded transmission line connects a radio frequency source to a gripping means such as the tip of a tweezer. In the present invention, a ground wire is connected to the transmission line near the gripping means.

In a preferred embodiment of the invention, the ground lead has one end connected to the shield of the transmission line near the gripping means, while the other end of the lead has a finger ring connected thereto. The ring is worn on a finger of an operator of the system during performance of the epilation.

Use of the system of the invention assures a positive ground of the tweezer and the patron, making it possible to remove the hair move quickly, speeding up the process of epilation. In addition, increased comfort is experienced by the patron. If the tweezer accidentally touches the patron, there is no danger of a burn, as is common with other devices.

BRIEF DESCRIPTION OF THE DRAWINGS

The sole FIGURE is an epilator system according to the invention, with a tweezers drawn in cross-section and a radio frequency source shown schematically.

DESCRIPTION OF THE PREFERRED EMBODIMENTS

The drawing illustrates an epilator system according to the invention, indicated generally by the reference numeral 10. Indicated schematically is a radio frequency electrical signal generator 12. A tweezer 14 is shown in cross-section. A shield transmission line or cable 15 is connected to transmit radio frequency energy from generator 12 to tweezer 14.

The tweezer 14 is a generally U-shaped device with arms 16 and 17. The arms are preferably of an electrically insulating material, such as plastic. Set in the end of the arms 16 and 17 are tweezer tips 20 and 21, respectively. These tips are electrically conducting, being formed, for example, of metal.

The rear portion 22 of tweezer 14 must have sufficient flexibility, so that arms 16 and 17 may be moved to press tips 20 and 21 together.

Cable 15 extends through rear portion 22 of tweezer 14 and through arm 17 to tip 21. The insertion of cable 15 in tweezer 14 can be accomplished by fabricating the tweezer from two complementary portions which fit together so as to form channels for the cable, for tips 20 and 21 and for a ground lead to be described. Cable 15 is shown as a coaxial cable with the center conductor 24 thereof connected to tip 21. The shield 26 of cable 15 is exposed inside arm 17 and has connected thereto a ground lead 28. Lead 28 runs through arm 17, emerging at the rear of tweezer 14. At the free end of ground lead 28 is a ring 30 of a suitable electrically conducting material such as copper.

In the operation of the system 10, tips 20 and 21 are used as gripping means to hold a hair (not shown) while radio frequency energy is passed from generator 12, through cable 15, and tip 21 to the hair. During this, the operator of the system wears ring 30 on a finger of either hand.

Tests have been conducted on the use of the improved epilator system 10. In the tests, a Derma-I Depilator manufactured by Electro-Kinetic Eng. & Mfg., Inc. was used. Hairs were removed both using lead 28 and ring 30 and not using the lead and ring.

In the first test, on very fine hair, a 0.55 mA setting was used. Five hairs were removed using ring 30, and the hairs were removable in an average time of 13.5 seconds. Five hairs removed without the ring were removable in an average of 26.6 seconds. Thus, without the ground lead and finger ring, the epilating time was increased 97%.

In a second test, a 0.52 mA setting was used. Twenty-five hairs removed, using the ring, were removable at an average time of 6.68 seconds. Twenty-five hairs removed without using the ring were removable at an average time of 11.88 seconds. Thus, failure to use the ground lead and ring resulted in a 77.8% increase in epilating time. In addition, the system used without the ground lead caused a tingling sensation in the patient, which was not felt when the ring was used.

In a third test, a 0.55 mA setting was again used, this time on normal leg hairs. With the ring, five hairs were removable in an average time of 13.6 seconds, while five hairs were removable at an average time of 18.2 seconds, not using the ground lead. In this case, then, the absence of the ground lead and ring caused a 33.8% increase in epilating time.

The foregoing tests quantify the observation that the system of the present invention renders a hair removable faster than the prior art system. In addition, and importantly in epilation, there is increased comfort for the patient with the use of the system of the invention.

Although preferred embodiments of the invention have been described in detail, it is to be understood that various changes, substitutions and alterations can be made therein, without departing from the spirit and scope of the invention as defined by the appended claims.

I claim:

1. In an epilator system of the type having a shielded transmission line connecting a radio frequency source to a conductive gripping means, the improvement comprising a ground lead connected to the transmission line shield near the gripping means, and a grounding means for connecting said ground lead to a ground during operation of the system, wherein said grounding means is adapted for connection to the body of an operator of the system during said operation.

2. In an epilator system of the type having a shield transmission line connecting a radio frequency source to a conductive gripping means, the improvement comprising a ground lead connected to the transmission line shield near the gripping means, and grounding means for connecting said ground lead to a ground during operation of the system, wherein said grounding means includes means for electrically connecting the lead to the hand of an operator of the system during said operation.

3. The system of claim 2, wherein said grounding means includes a conductive finger ring.

4. An epilator system, comprising:
   a tweezer including a plurality of arms with a conductive tip on each of said arms;
   a radio frequency generator;
   a cable having a shield and being connected at one end to the generator and, at the other end, passing through one of said arms and connected to the tip associated with the one arm;
   a lead having one end connected to the cable shield in said one arm; and
   a conductive finger ring connected to the other end of the lead.

* * * * *